US00PP16612P3

(12) United States Plant Patent
Lim

(10) Patent No.: US PP16,612 P3
(45) Date of Patent: Jun. 6, 2006

(54) SHRUB ROSE PLANT NAMED 'BAIEYE'

(50) Latin Name: *Rosa hybrida*
Varietal Denomination: BAIeye

(75) Inventor: Peter P. Lim, Yamhill, OR (US)

(73) Assignee: Bailey Nurseries, Inc., St. Paul, MN (US)

( * ) Notice: Subject to any disclaimer, the term of this patent is extended or adjusted under 35 U.S.C. 154(b) by 122 days.

(21) Appl. No.: 10/962,443

(22) Filed: Oct. 13, 2004

(65) Prior Publication Data

US 2006/0090226 P1 Apr. 27, 2006

(51) Int. Cl.
*A01H 5/00* (2006.01)

(52) U.S. Cl. ..... Plt./108

(58) Field of Classification Search ..... Plt./108
See application file for complete search history.

*Primary Examiner*—Anne Marie Grunberg
*Assistant Examiner*—Annette H Para
(74) *Attorney, Agent, or Firm*—Buchanan Ingersoll PC

(57) ABSTRACT

A new and distinct variety of landscape shrub rose plant is provided which abundantly forms during June and on a recurrent basis thereafter single bold red blossoms having a golden eye. The blossoms also display a mild rose fragrance. The plant exhibits a compact, dense and bushy growth habit, attractive semi-glossy dark green foliage that initially bears a tint of red-purple, and good tolerance to Black Spot and Powdery Mildew. The attractive dark green semi-glossy foliage contrasts nicely with the bold red blossom coloration. The new variety is particularly well suited for growing as attractive ornamentation in parks and gardens.

2 Drawing Sheets

Botanical commercial classification: *Rosa hybrida*/Shrub Rose Plant.
Varietal denomination: cv. 'BAIeye'.

SUMMARY OF THE INVENTION

The new variety of *Rosa hybrida* landscape shrub rose plant was created at Yamhill, Oreg., U.S.A., during 1997 by artificial pollination wherein two parents were crossed which previously had been studied in the hope that they would contribute the desired characteristics. The female parent (i.e., the seed parent) was an unreleased *Rosa* plant from my breeding program that was designated 'R92108' (non-patented in the United States). The male parent (i.e., the pollen parent) was the 'KORfungo' variety (non-patented in the United States). The 'KORfungo' variety sometimes is known as the 'Royal Bassino' variety. The parentage of the new variety can be summarized as follows:

'R92108'×'KORfungo'.

The seeds resulting from the above pollination were sown and plants were obtained which were physically and biologically different from each other. Selective study resulted in the identification during 1999 of a single plant of the new variety having the distinctive ornamental characteristics hereafter described.

It was found that the new variety of the present invention:

(a) exhibits a compact, dense and bushy growth habit, (b) abundantly forms during June and on a recurrent basis thereafter attractive single bold red blossoms having a golden eye, (c) forms attractive semi-glossy dark green foliage when mature that initially bears a tint of red-purple, (d) is highly tolerant to Black Spot and Powdery Mildew; and (e) is particularly well suited for growing as attractive ornamentation in parks and gardens.

The new variety well meets the needs of the horticultural industry and can be grown to advantage in the landscape where attractive ornamentation is desired. The bold red blossoms having a golden eye contrast nicely with the semi-glossy dark green foliage. The yellow pollen contributes to the appearance of the golden eye. A tough shrub rose that can be grown in U.S.D.A. Hardiness Zone Nos. 4 to 9 is provided.

The new variety can be readily distinguished from other varieties including its ancestors. For instance, the 'R92108' variety forms considerably larger double blossoms that are deep pink in coloration, and the 'KORfungo' variety forms dark red semi-double blossoms on semi-pendulous canes and bears light green foliage. The new variety also can be readily distinguished from the 'Henry Kelsey' (non-patented in the United States) and 'RADrazz' (U.S. Plant Pat. No. 11,836) varieties. The 'Henry Kelsey' variety forms considerably larger double medium red blossoms and glossy foliage. The 'RADrazz' variety forms considerably larger single blossoms that are red with a dark pink tint.

The new variety beginning in August 1998 has been found to undergo asexual propagation by budding on an understock and by the rooting of cuttings. 'Dr. Huey' rootstock was used during the budding. Such asexual propagation by these techniques at Yamhill, Oreg., U.S.A., St. Paul, Minn., U.S.A., and at Phoenix, Ariz., U.S.A. has shown that the characteristics of the new variety are stable and are strictly transmissible by such asexual propagation from one generation to another. Accordingly, the new variety reproduces true to type. The new variety grows well on its own roots.

Initially the new plant was designated 97R327. The new plant subsequently has been named the 'BAIeye' variety, and currently is being marketed while using the GARDEN JUBILEE and GOLDEN EYE trademarks.

BRIEF DESCRIPTION OF THE PHOTOGRAPHS

The accompanying photographs show as nearly true as it is reasonably possible to make the same in color illustrations of this character, typical specimens of the new variety. The rose plants of the new variety had been propagated by the rooting of cuttings, were approximately two and three years of age, and were being grown outdoors during the 2003 season at St. Paul, Minn., U.S.A., and at Yamhill, Oreg., U.S.A.

DETAILED DESCRIPTION

Figure 1:
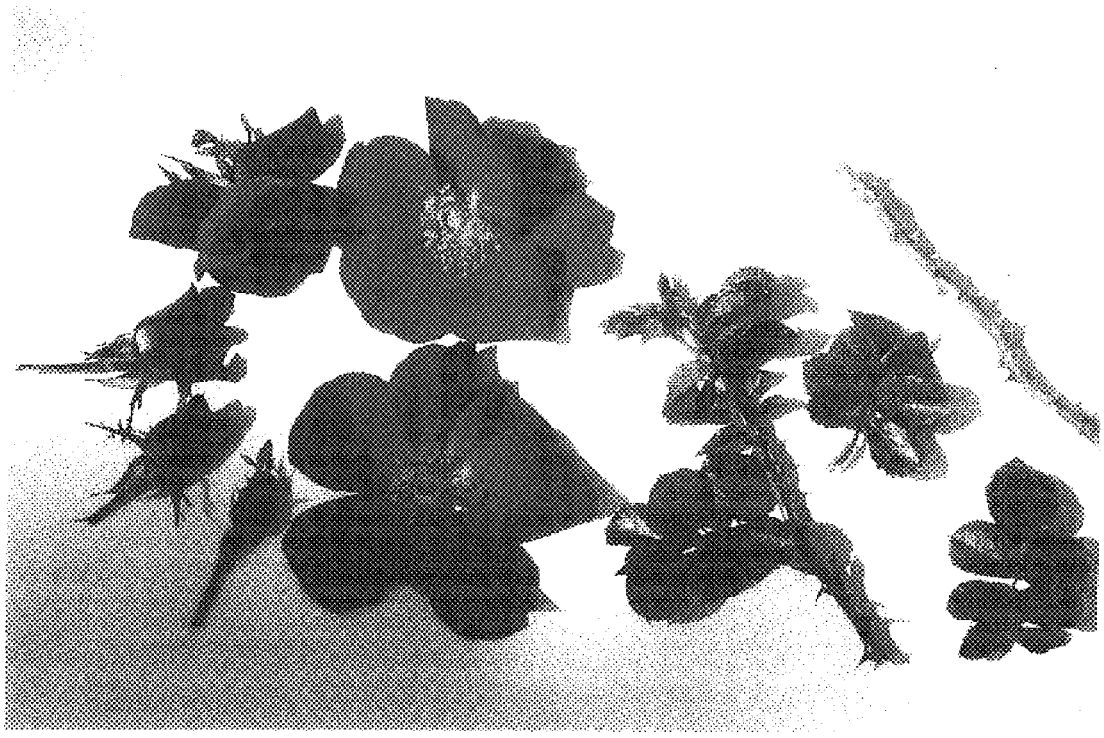
FIG. 1 illustrates typical plant parts of the new variety including buds in various stages of opening, a newly-opened blossom, mature blossoms, a new shoot with foliage, seven-leaflet leaves, and a stem.
Figure 2:
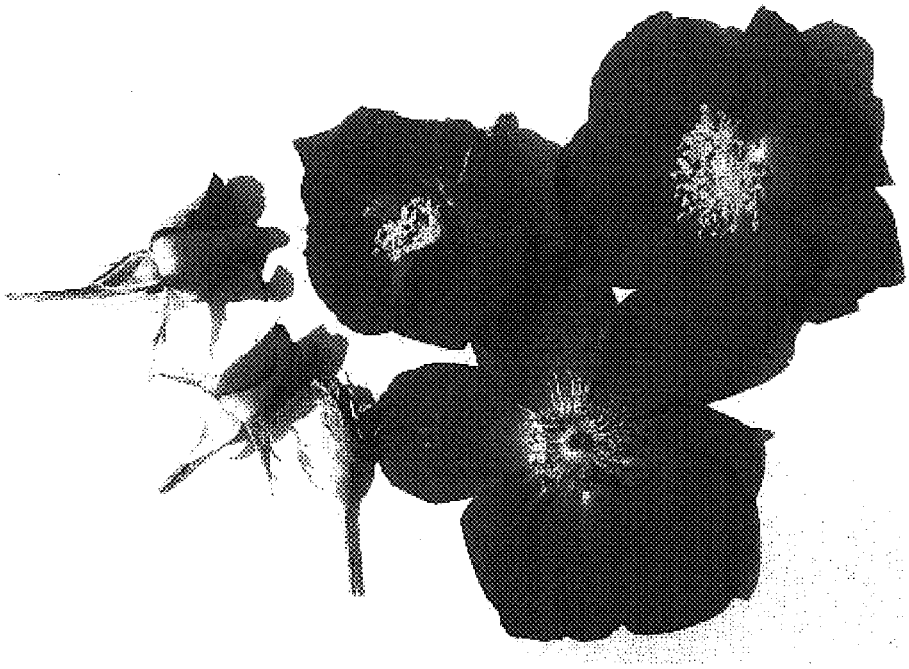
FIG. 2 illustrates typical buds and blossoms at various stages of maturity.
Figure 3:
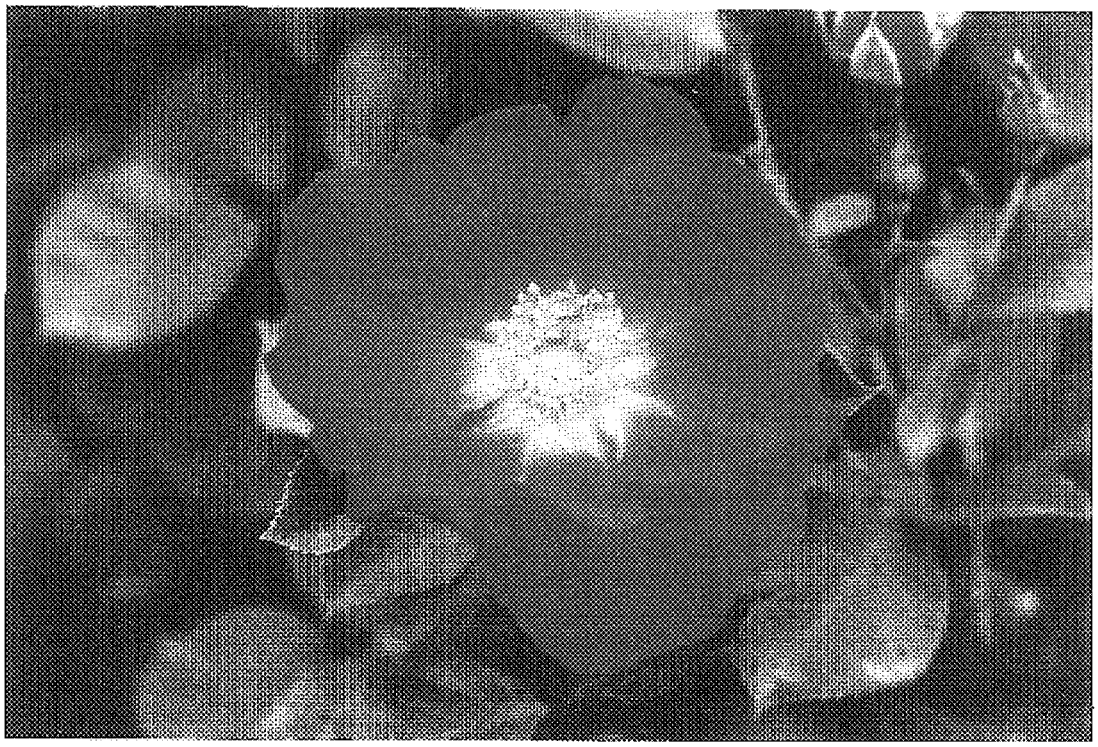
FIG. 3 illustrates a typical fully-opened bold red blossom with a golden eye.

The chart used in the identification of the colors is that of The Royal Horticultural Society (R.H.S. Colour Chart). Common color terms are to be accorded their ordinary dictionary significance. The description is based on the observation of two and three year-old plants while grown outdoors on their own roots during June and July 2003, at St. Paul, Minn., U.S.A., and during June 2004 at Phoenix, Ariz., U.S.A.

Botanical classification: *Rosa hybrida,* var. 'BAIeye'.
Class: Landscape Shrub.
Plant:
- *Height.*—Approximately 60 cm to 1 m at the end of the growing season.
- *Width.*—Approximately 60 cm on average at the end of the growing season.
- *Habit.*—Compact, bushy, and upright rounded.

Branches:
- *Color.*—Young stems: Yellow-Green Group 146B and 146C suffused with Greyed-Purple Group 185B. Adult wood: Grey-Brown Group 199B with streaks of Brown Group 200C.
- *Thorns.*—Size: approximately 1 cm in length on average. Color: Red Group 53A suffused with some Yellow-Green Group 146B.

Leaves:
- *Stipules.*—Generally parallel with the auricle facing outward.
- *Petioles.*—Upper surface: Yellow-Green Group 146B with highlights of Greyed-Purple Group 185B. Under surface: Yellow-Green Group 144A and 144B.
- *Leaflets.*—Number: 3, 5 (most often), and 7. Shape: ovate with a rounded base and an acuminate tip. Serration: serrulate. Texture: bears a semi-glossy finish. General appearance: dark green with a semi-glossy surface when mature. Color (young foliage): upper surface: Yellow-Green Group 146A with highlights of Greyed-Purple Group 184A. Under surface: between Yellow-Green Group 146B and 146C with highlights of Greyed-Purple Group 184B. Color (adult foliage): upper surface: Yellow-Green Group 147A. Under surface: between Yellow-Green Group 146A with highlights of Greyed-Purple Group 185B.

Inflorescence:
- *Number of flowers.*—Commonly approximately 5 blooms in a cluster on average per lateral stem.
- *Peduncle.*—Between Yellow-Green Group 144A and 144B.
- *Sepals.*—Upper surface: commonly Yellow-Green Group 144B blended with Green Group 143A and 143B. Under surface: Yellow-Green Group 144B blended with Yellow-Green Group 144A and 145B and with some pubescence. Size: approximately 2.5 cm in length.
- *Buds.*—Shape: generally pointed. Size: medium. Length: approximately 2.0 cm on average. Diameter: approximately 1.25 cm on average. Color: upper petal surface: between Greyed-Purple Group 185A and Red Group 53B. Under petal surface: Red Group 53B.
- *Flower.*—Shape: single. Diameter: approximately 5.0 cm on average. Color (when opening begins): upper surface: between Red Group 45A and 45B blending with Yellow-Green Group 154A toward the basal petal spot. Under surface: Red Group 46C blending to Yellow Group 5A and 5B toward the basal petal spot. Color (when blooming): upper surface: Red Group 45B blending to Yellow Group 5A and 5B toward the basal petal spot. Under surface: Red Group 45D blending to Yellow Group 4C toward the basal petal spot. Color (at end of blooming): upper surface: Red Group 46C blending to Yellow Group 5B toward the basal petal spot. Under surface: Red Group 54A blending to Yellow Group 4C toward the basal petal spot. Color (basal petal spot): Yellow-Orange Group 15A. Fragrance: mild rose. Lasting quality: the blossoms commonly last approximately 5 days on average depending upon the temperature and sunlight exposure. Petal number: commonly approximately 7 to 10, and approximately 8 on average under normal growing conditions. Petal shape: wedge-shaped commonly with a curled apex and a slightly ruffled edge when fully open. Petal drop: commonly the petals detach cleanly at full blossom maturity. Anthers: Yellow-Orange Group 21B in coloration. Filament number: commonly approximately 144 on average. Filament color: Yellow-Orange Group 20A in coloration. Pollen: yellow in coloration and contributes to the appearance of the golden eye. Pistils: approximately 61 on average. Stigmas: Yellow-Orange Group 15C in coloration. Styles: Yellow-Green Group 154B with some highlights of Red Group 41A in coloration.

Development:
- *Vegetation.*—Compact and dense.
- *Blooming.*—Heavily during June and recurrently during the season.
- *Resistance to diseases.*—Highly tolerant to Black Spot, and Powdery Mildew.
- *Hardiness zone.*—U.S.D.A. Hardiness Zone Nos. 4 to 9.

I claim:

1. A new and distinct variety of landscape shrub rose plant characterized by the following combination of characteristics:

(a) exhibits a compact, dense and bushy growth habit, (b) abundantly forms during June and on a recurrent basis thereafter attractive single bold red blossoms having a golden eye, (c) forms attractive semi-glossy dark green foliage when mature that initially bears a tint of red-purple, (d) is highly tolerant to Black Spot and Powdery Mildew, and (e) is particularly well suited for growing as attractive ornamentation in parks and gardens;

substantially as herein shown and described.

* * * * *